US010845768B2

(12) United States Patent
Gervais et al.

(10) Patent No.: US 10,845,768 B2
(45) Date of Patent: *Nov. 24, 2020

(54) ENVIRONMENT CONTROLLER AND METHOD FOR INFERRING VIA A NEURAL NETWORK ONE OR MORE COMMANDS FOR CONTROLLING AN APPLIANCE

(71) Applicant: DISTECH CONTROLS INC., Brossard (CA)

(72) Inventors: Francois Gervais, Lachine (CA); Carlo Masciovecchio, St-Isidore-de-Laparairie (CA); Dominique Laplante, St-Dominique (CA)

(73) Assignee: DISTECH CONTROLS INC., Brossard (CA)

( * ) Notice: Subject to any disclaimer, the term of this patent is extended or adjusted under 35 U.S.C. 154(b) by 50 days.

This patent is subject to a terminal disclaimer.

(21) Appl. No.: 15/839,068

(22) Filed: Dec. 12, 2017

(65) Prior Publication Data
US 2019/0179269 A1 Jun. 13, 2019

(51) Int. Cl.
*G05B 13/02* (2006.01)
*H04L 12/28* (2006.01)
(Continued)

(52) U.S. Cl.
CPC .......... *G05B 13/0265* (2013.01); *F24F 11/30* (2018.01); *F24F 11/62* (2018.01);
(Continued)

(58) Field of Classification Search
CPC ..... G05B 13/0265; G05B 17/02; F24F 11/76; F24F 11/30; F24F 11/62; G05D 23/1927;
(Continued)

(56) References Cited

U.S. PATENT DOCUMENTS 5,257,735 A * 11/1993 Takahashi ........... F24F 11/00 236/44 A
7,156,316 B2 * 1/2007 Kates ................. G05D 23/1934 236/1 B
(Continued)

FOREIGN PATENT DOCUMENTS

WO 2017076433 A1 5/2017
WO WO-2017076433 A1 * 5/2017 ......... B60H 1/00742
WO WO-2018200225 A1 * 11/2018 ............. F24F 11/63

*Primary Examiner* — Crystal J Barnes-Bullock
(74) *Attorney, Agent, or Firm* — RatnerPrestia

(57) ABSTRACT

Method and environment controller for inferring via a neural network one or more commands for controlling an appliance. A predictive model generated by a neural network training engine is stored by the environment controller. The environment controller receives at least one environmental characteristic value (for example, at least one of a current temperature, current humidity level, current carbon dioxide level, and current room occupancy). The environment controller receives at least one set point (for example, at least one of a target temperature, target humidity level, and target carbon dioxide level). The environment controller executes a neural network inference engine, which uses the predictive model for inferring the one or more commands for controlling the appliance based on the at least one environmental characteristic value and the at least one set point. The environment controller transmits the one or more commands to the controlled appliance.

19 Claims, 5 Drawing Sheets

(51) Int. Cl.
*G05B 17/02* (2006.01)
*G06N 5/04* (2006.01)
*G01N 33/00* (2006.01)
*F24F 11/30* (2018.01)
*F24F 11/62* (2018.01)
*F24F 11/76* (2018.01)
*G06N 3/08* (2006.01)
*G06F 9/451* (2018.01)
*G01S 17/04* (2020.01)

(52) U.S. Cl.
CPC ............ *F24F 11/76* (2018.01); *G01N 33/004* (2013.01); *G01S 17/04* (2020.01); *G05B 17/02* (2013.01); *G06F 9/451* (2018.02); *G06N 3/084* (2013.01); *G06N 5/04* (2013.01); *H04L 12/2816* (2013.01); *H04L 12/2827* (2013.01)

(58) Field of Classification Search
CPC ...... G06N 5/04; G06N 3/084; H04L 12/2877; H04L 12/2827; H04L 12/2816; G06F 9/451; G01N 33/004; G01S 17/026
See application file for complete search history.

(56) References Cited

U.S. PATENT DOCUMENTS

| | | | | |
|---|---|---|---|---|
| 7,839,275 B2* | 11/2010 | Spalink | ............ | G05D 23/1931 340/501 |
| 7,840,310 B2* | 11/2010 | Orfield | ............ | F24F 11/62 700/275 |
| 8,010,237 B2* | 8/2011 | Cheung | ............ | G05B 13/0245 700/278 |
| 8,412,654 B2* | 4/2013 | Montalvo | ............ | H02J 3/14 307/31 |
| 8,457,796 B2* | 6/2013 | Thind | ............ | G05B 15/02 236/47 |
| 8,849,471 B2* | 9/2014 | Daniel | ............ | H04L 12/40045 700/293 |
| 9,190,844 B2* | 11/2015 | Tran | ............ | H02J 3/14 |
| 9,477,239 B2* | 10/2016 | Bergman | ............ | G05D 23/19 |
| 9,594,384 B2* | 3/2017 | Bergman | ............ | F24F 11/30 |
| 9,651,929 B2* | 5/2017 | Horesh | ............ | G06Q 50/06 |
| 9,671,843 B2* | 6/2017 | Ellis | ............ | H02J 3/14 |
| 9,905,122 B2* | 2/2018 | Sloo | ............ | F24F 11/30 |
| 10,360,779 B2* | 7/2019 | Correnti | ............ | G08B 25/08 |
| 10,373,082 B2* | 8/2019 | Henze | ............ | G06Q 10/04 |
| 2002/0144537 A1* | 10/2002 | Sharp | ............ | G01N 1/26 73/31.01 |
| 2003/0160103 A1* | 8/2003 | Guo | ............ | G05D 23/1917 236/47 |
| 2007/0114292 A1 | 5/2007 | Breed et al. | | |
| 2007/0119958 A1* | 5/2007 | Kates | ............ | G05D 23/1934 236/1 B |
| 2008/0001712 A1* | 1/2008 | Agarwal | ............ | G06Q 10/087 340/10.1 |
| 2008/0281472 A1* | 11/2008 | Podgorny | ............ | G05B 15/02 700/276 |
| 2010/0088261 A1* | 4/2010 | Montalvo | ............ | H02J 3/14 706/15 |
| 2011/0113360 A1* | 5/2011 | Johnson | ............ | H04L 12/2825 715/771 |
| 2011/0295430 A1* | 12/2011 | Kouninski | ............ | G05D 23/1906 700/278 |
| 2012/0144057 A1* | 6/2012 | Meredith | ............ | H04L 63/0263 709/232 |
| 2012/0245740 A1 | 9/2012 | Raestik et al. | | |
| 2013/0013121 A1* | 1/2013 | Henze | ............ | G06Q 10/04 700/291 |
| 2014/0277757 A1* | 9/2014 | Wang | ............ | G05D 23/1927 700/276 |
| 2014/0321839 A1* | 10/2014 | Armstrong | ............ | G05D 23/1951 392/463 |
| 2015/0248118 A1* | 9/2015 | Li | ............ | F24F 11/30 700/295 |
| 2015/0293504 A1 | 10/2015 | Blum et al. | | |
| 2015/0296594 A1 | 10/2015 | Blum et al. | | |
| 2015/0369503 A1* | 12/2015 | Flaherty | ............ | F24F 11/30 700/277 |
| 2016/0091904 A1* | 3/2016 | Horesh | ............ | F24F 11/30 700/276 |
| 2017/0108236 A1* | 4/2017 | Guan | ............ | G05B 19/04 |
| 2018/0100662 A1* | 4/2018 | Farahmand | ............ | F24F 11/62 |
| 2018/0195911 A1* | 7/2018 | Kakade | ............ | G01K 13/02 |
| 2018/0268220 A1* | 9/2018 | Lee | ............ | G06K 9/4604 |
| 2018/0299153 A1* | 10/2018 | Ajax | ............ | G05B 15/02 |
| 2018/0328967 A1* | 11/2018 | Lange | ............ | G01R 21/133 |
| 2018/0364654 A1* | 12/2018 | Locke | ............ | G05B 13/0265 |
| 2018/0367483 A1* | 12/2018 | Rodriguez | ............ | H04L 51/046 |
| 2018/0375444 A1* | 12/2018 | Gamroth | ............ | H02N 2/188 |
| 2019/0017719 A1* | 1/2019 | Sinha | ............ | G05B 15/02 |
| 2019/0126472 A1* | 5/2019 | Tunyasuvunakool | ... | B25J 9/163 |
| 2019/0140856 A1* | 5/2019 | Choi | ............ | H04L 12/2809 |

* cited by examiner

ENVIRONMENT CONTROLLER AND METHOD FOR INFERRING VIA A NEURAL NETWORK ONE OR MORE COMMANDS FOR CONTROLLING AN APPLIANCE

TECHNICAL FIELD

The present disclosure relates to the field of environment control systems. More specifically, the present disclosure relates to an environment controller and a method for inferring via a neural network one or more commands for controlling an appliance.

BACKGROUND

Systems for controlling environmental conditions, for example in buildings, are becoming increasingly sophisticated. A control system may at once control heating and cooling, monitor air quality, detect hazardous conditions such as fire, carbon monoxide release, intrusion, and the like. Such control systems generally include at least one environment controller, which receives measured environmental characteristic values, generally from external sensors, and in turn determines set points or command parameters to be sent to controlled appliances.

For instance, a room has current environmental characteristic values, such as a current temperature and a current humidity level, detected by sensors and reported to an environment controller. A user interacts with the environment controller to provide set point(s), such as a target temperature and/or a target humidity level. The environment controller sends the set point(s) to a controlled appliance (e.g. a heating, ventilating, and/or air-conditioning (HVAC) appliance). The controlled appliance generates commands for actuating internal components (of the controlled appliance) to reach the set point(s). Alternatively, the environment controller directly determines command(s) based on the set point(s), and transmits the command(s) to the controlled appliance. The controlled appliance uses the command(s) received from the environment controller to actuate the internal components to reach the set point(s). Examples of internal components include a motor, an electrical circuit (e.g. for generating heat), a valve (e.g. for controlling an air flow), etc.

However, the generation of the command(s) for actuating internal components of the controlled appliance does not take into consideration the current environmental characteristic values and the set point(s) in combination, to generate the most adequate command(s). The adequacy of the command(s) depends on one or more criteria, which can be taken into consideration individually or in combination. Examples of such criteria include a comfort of the people present in the room, stress imposed on components of the controlled appliance (e.g. mechanical stress, heating stress, etc.), energy consumption, etc.

For instance, we take the example where the current environmental characteristic values include the current temperature of the room and the set points include the target temperature of the room. In the case of a significant difference between the current temperature and the target temperature (e.g. more than 5 degrees Celsius), the comfort of the people in the room shall be of prime importance. Thus, the generated command(s) shall provide for a quick convergence from the current temperature to the target temperature. However, this quick convergence may induce an increase of the stress imposed on components of the controlled appliance and a significant energy consumption. By contrast, in the case of a small difference between the current temperature and the target temperature (e.g. less than 5 degrees Celsius), the comfort of the people in the room is not affected in a significant manner by the speed at which the convergence from the current temperature to the target temperature is achieved. Therefore, the generated command(s) shall aim at preserving the controlled appliance (by minimizing the stress imposed on components of the controlled appliance) and minimizing energy consumption.

A set of rules taking into consideration the current environmental characteristic values and the set point(s) may be implemented by the environment controller, for generating the most adequate command(s). However, the criteria for evaluating the adequacy of the command(s) based on the current environmental characteristic values and the set point(s) are multiple, potentially complex, and generally inter-related. Thus, the aforementioned set of rules would either be too simple to generate an effective model for generating the most adequate command(s), or alternatively too complicated to be designed by a human being.

However, current advances in artificial intelligence, and more specifically in neural networks, can be taken advantage of. More specifically, a model, taking into consideration the current environmental characteristic values and the set point(s) to generate the most adequate command(s) for controlling the appliance, can be generated and used by a neural network.

Therefore, there is a need for a new environment controller and method for inferring via a neural network one or more commands for controlling an appliance.

SUMMARY

According to a first aspect, the present disclosure relates to an environment controller. The environment controller comprises a communication interface, memory for storing a predictive model generated by a neural network training engine, and a processing unit. The processing unit receives at least one environmental characteristic value via the communication interface. The processing unit receives at least one set point via at least one of the communication interface and a user interface of the environment controller. The processing unit executes a neural network inference engine. The neural network inference engine uses the predictive model for inferring one or more commands for controlling an appliance based on the at least one environmental characteristic value and the at least one set point. The processing unit transmits the one or more commands to the controlled appliance via the communication interface.

According to a second aspect, the present disclosure relates to a method for inferring via a neural network one or more commands for controlling an appliance. The method comprises storing a predictive model generated by a neural network training engine in a memory of an environment controller. The method comprises receiving, by a processing unit of the environment controller, at least one environmental characteristic value via a communication interface of the environment controller. The method comprises receiving, by the processing unit, at least one set point via at least one of the communication interface and a user interface of the environment controller. The method comprises executing, by the processing unit, a neural network inference engine. The neural network inference engine uses the predictive model for inferring the one or more commands for controlling the appliance based on the at least one environmental characteristic value and the at least one set point. The method comprises transmitting, by the processing unit, the one or more commands to the controlled appliance via the communication interface.

According to a third aspect, the present disclosure relates to a non-transitory computer program product comprising instructions executable by a processing unit of an environment controller. The execution of the instructions by the processing unit of the environment controller provides for inferring via a neural network one or more commands for controlling an appliance. More specifically, the execution of the instructions provides for storing a predictive model generated by a neural network training engine in a memory of the environment controller. The execution of the instructions provides for receiving by the processing unit at least one environmental characteristic value via a communication interface of the environment controller. The execution of the instructions provides for receiving, by the processing unit, at least one set point via at least one of the communication interface and a user interface of the environment controller. The execution of the instructions provides for executing, by the processing unit, a neural network inference engine. The neural network inference engine uses the predictive model for inferring the one or more commands for controlling the appliance based on the at least one environmental characteristic value and the at least one set point. The execution of the instructions provides for transmitting, by the processing unit, the one or more commands to the controlled appliance via the communication interface.

BRIEF DESCRIPTION OF THE DRAWINGS

Embodiments of the disclosure will be described by way of example only with reference to the accompanying drawings, in which.

DETAILED DESCRIPTION

The foregoing and other features will become more apparent upon reading of the following non-restrictive description of illustrative embodiments thereof, given by way of example only with reference to the accompanying drawings.

Various aspects of the present disclosure generally address one or more of the problems related to an optimization of command(s) sent by an environment controller to a controlled appliance based on current environmental conditions and target environmental conditions (also referred to as set points in the present disclosure).

TERMINOLOGY

The following terminology is used throughout the present disclosure:

Environment: condition(s) (temperature, humidity, pressure, oxygen level, carbon dioxide level, light level, security, etc.) prevailing in a controlled area or place, such as for example in a building.

Environment control system: a set of components which collaborate for monitoring and controlling an environment.

Environmental data: any data (e.g. information, commands) related to an environment that may be exchanged between components of an environment control system.

Environment control device (ECD): generic name for a component of an environment control system. An ECD may consist of an environment controller, a sensor, a controlled appliance, etc.

Environment controller: device capable of receiving information related to an environment and sending commands based on such information.

Environmental characteristic: measurable, quantifiable or verifiable property of an environment.

Environmental characteristic value: numerical, qualitative or verifiable representation of an environmental characteristic.

Sensor: device that detects an environmental characteristic and provides a numerical, quantitative or verifiable representation thereof. The numerical, quantitative or verifiable representation may be sent to an environment controller.

Controlled appliance: device that receives a command and executes the command. The command may be received from an environment controller.

Environmental state: a current condition of an environment based on an environmental characteristic, each environmental state may comprise a range of values or verifiable representation for the corresponding environmental characteristic.

VAV appliance: A Variable Air Volume appliance is a type of heating, ventilating, and/or air-conditioning (HVAC) system. By contrast to a Constant Air Volume (CAV) appliance, which supplies a constant airflow at a variable temperature, a VAV appliance varies the airflow at a constant temperature.

Figure 1:
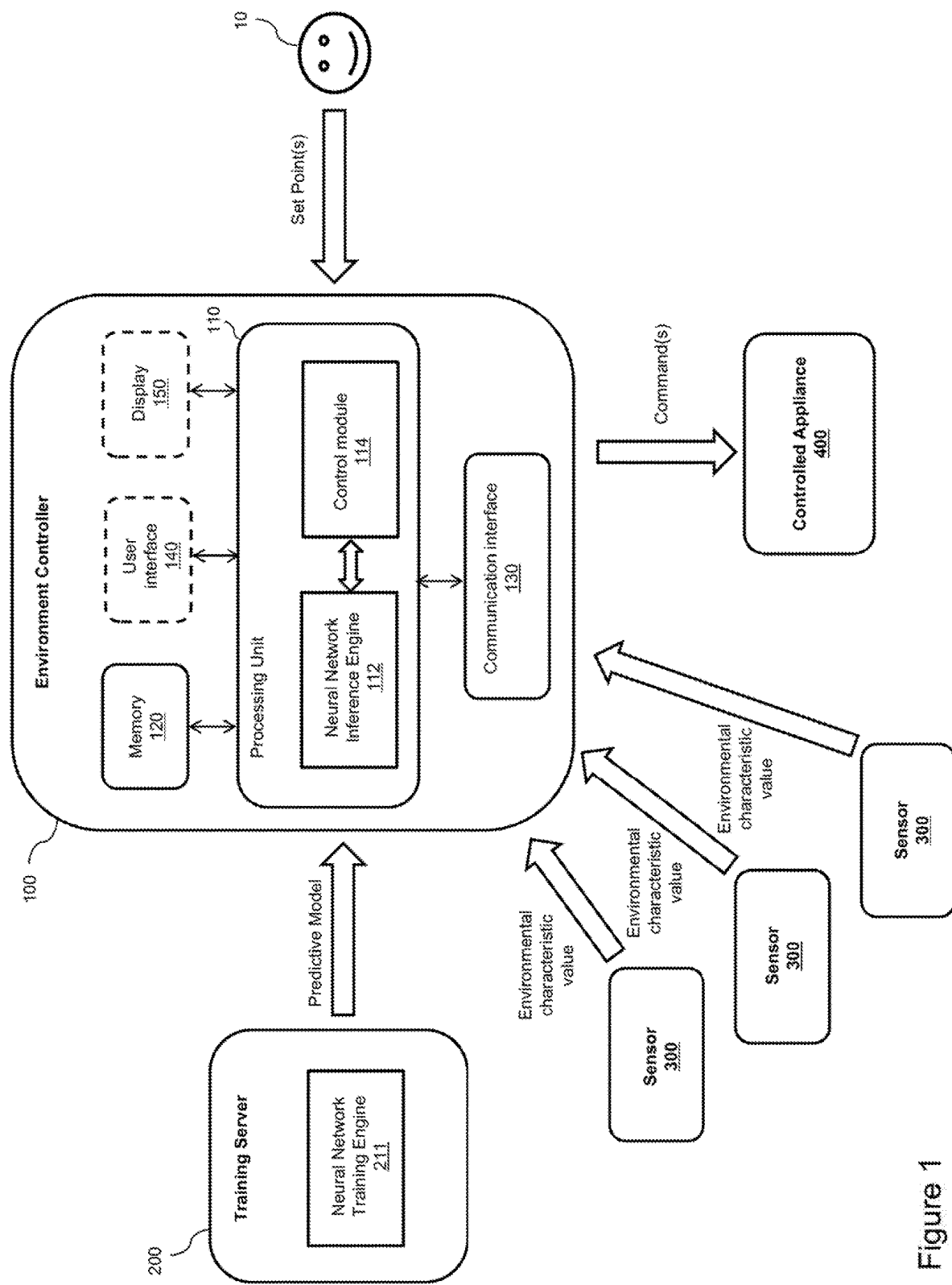
FIG. 1 illustrates an environment controller capable of inferring via a neural network one or more commands for controlling an appliance.
Figure 2:
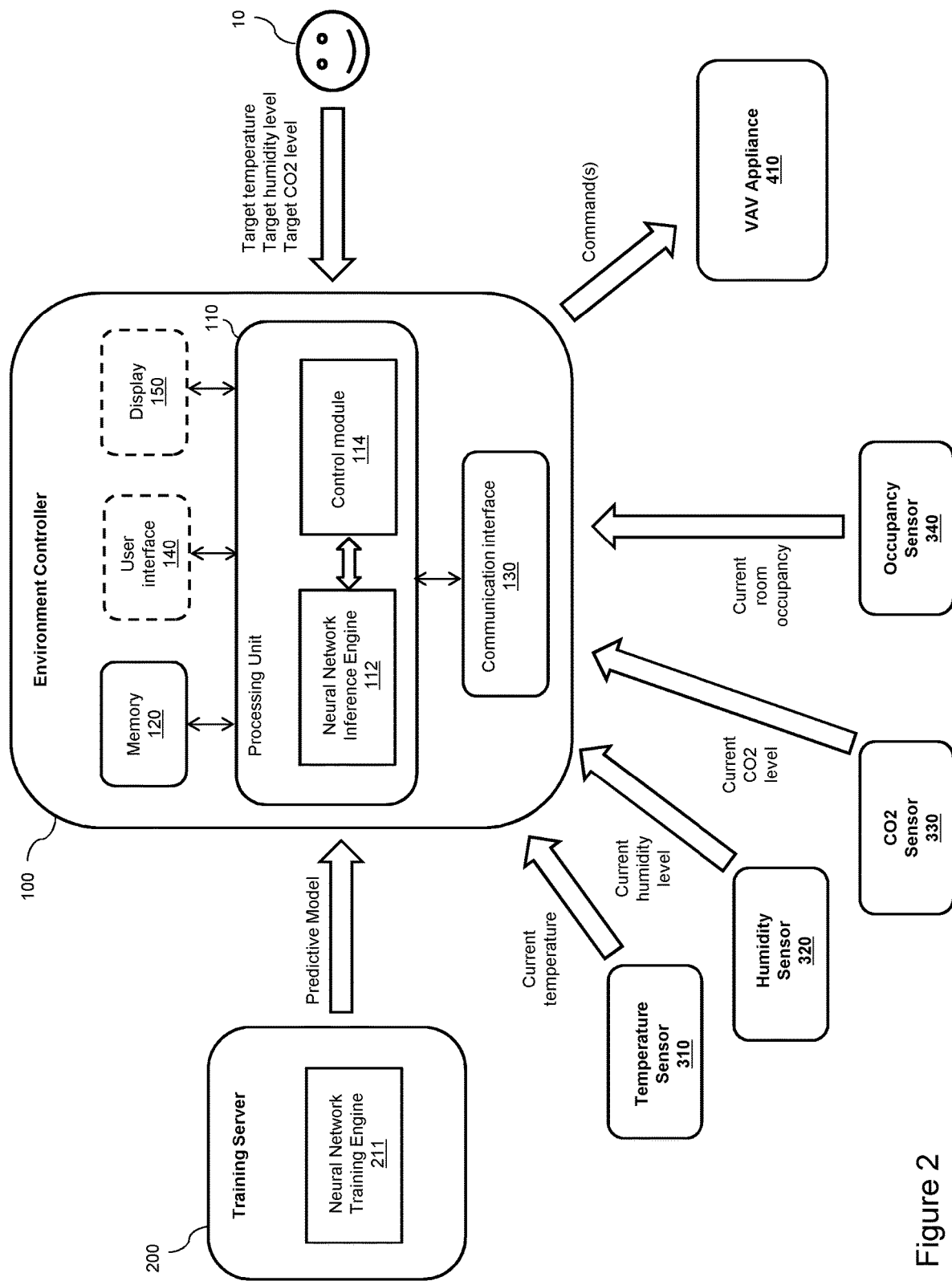
FIG. 2 illustrates an exemplary environment control system where the environment controller of FIG. 1 is deployed.
Figure 3:
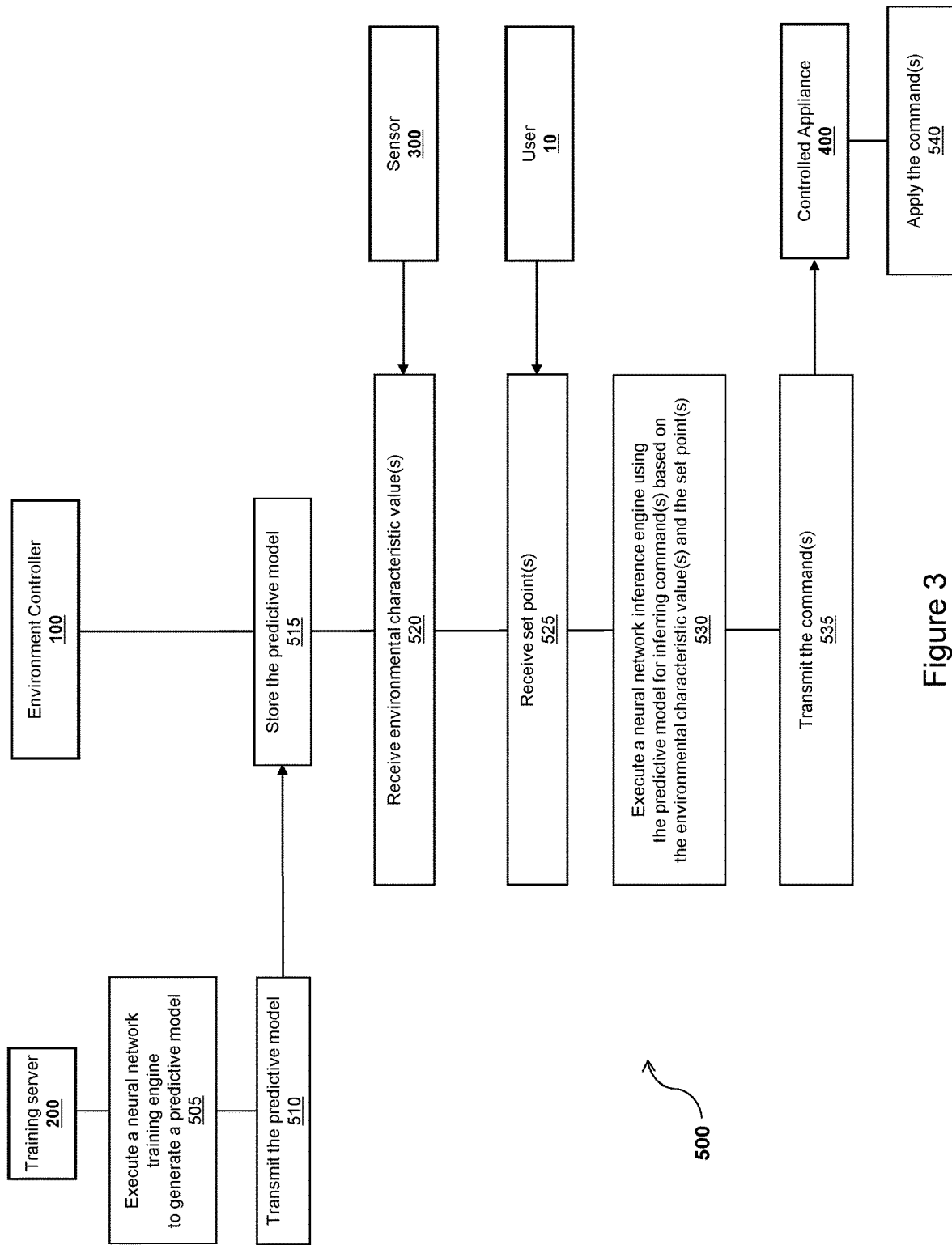
FIG. 3 illustrates a method implemented by the environment controller of FIGS. 1 and 2 for inferring via a neural network one or more commands for controlling the appliance of FIGS. 1 and 2.

Referring now concurrently to FIGS. 1, 2 and 3, an environment controller 100 (represented in FIGS. 1 and 2) and a method 500 (represented in FIG. 3) for inferring via a neural network one or more commands for controlling an appliance are illustrated.

The environment controller 100 comprises a processing unit 110, memory 120, a communication interface 130, optionally a user interface 140, and optionally a display 150. The environment controller 100 may comprise additional components not represented in FIG. 1 for simplification purposes.

The processing unit 110 comprises one or more processors (not represented in FIG. 1) capable of executing instructions of a computer program. Each processor may further comprise one or several cores.

The memory 120 stores instructions of computer program(s) executed by the processing unit 110, data generated by the execution of the computer program(s), data received via the communication interface 130, data received via the optional user interface 140, etc. Only a single memory 120 is represented in FIG. 1, but the environment controller 100 may comprise several types of memories, including volatile memory (such as a volatile Random Access Memory (RAM)) and non-volatile memory (such as a hard drive).

The communication interface 130 allows the environment controller 100 to exchange data with several devices (e.g. a training server 200, one or more sensors 300, one or more controlled appliances 400, etc.) over one or more communication network (not represented in FIG. 1 for simplification purposes). The term communication interface 130 shall be interpreted broadly, as supporting a single communication standard/technology, or a plurality of communication standards/technologies. Examples of communication interfaces 130 include a wireless (e.g. Wi-Fi, cellular, wireless mesh, etc.) communication module, a wired (e.g. Ethernet) communication module, a combination of wireless and wired communication modules, etc. In an exemplary configuration, the communication interface 130 of the environment controller 100 has a first wireless (e.g. Wi-Fi) communication module for exchanging data with the sensor(s) and the controlled appliance(s), and a second wired (e.g. Ethernet) communication module for exchanging data with the training server 200.

At least some of the steps of the method 500 are implemented by the environment controller 100, to infer via a neural network one or more commands for controlling the controlled appliance 400.

A dedicated computer program has instructions for implementing at least some of the steps of the method 500. The instructions are comprised in a non-transitory computer program product (e.g. the memory 120) of the environment controller 100. The instructions provide for inferring via a neural network one or more commands for controlling the controlled appliance 400, when executed by the processing unit 110 of the environment controller 100. The instructions are deliverable to the environment controller 100 via an electronically-readable media such as a storage media (e.g. CD-ROM, USB key, etc.), or via communication links (e.g. via a communication network through the communication interface 130).

The dedicated computer program executed by the processing unit 110 comprises a neural network inference engine 112 and a control module 114.

Also represented in FIG. 1 is the training server 200. Although not represented in FIG. 1 for simplification purposes, the training server 200 comprises a processing unit, memory and a communication interface. The processing unit of the training server 200 executes a neural network training engine 211.

The execution of the neural network training engine 211 generates a predictive model, which is transmitted to the environment controller 100 via the communication interface of the training server 200. For example, the predictive model is transmitted over a communication network and received via the communication interface 130 of the environment controller 100.

Also represented in FIG. 1 are the sensors 300. Although not represented in FIG. 1 for simplification purposes, the sensors 300 comprise at least one sensing module for detecting an environmental characteristic, and a communication interface for transmitting to the environment controller 100 an environmental characteristic value corresponding to the detected environmental characteristic. The environmental characteristic value is transmitted over a communication network and received via the communication interface 130 of the environment controller 100.

FIG. 2 illustrates examples of sensors 300 and corresponding examples of transmitted environmental characteristic value(s). The examples include a temperature sensor 310, capable of measuring a current temperature and transmitting the measured current temperature to the environment controller 100. The examples also include a humidity sensor 320, capable of measuring a current humidity level and transmitting the measured current humidity level to the environment controller 100. The examples further include a carbon dioxide ($CO_2$) sensor 330, capable of measuring a current $CO_2$ level and transmitting the measured current $CO_2$ level to the environment controller 100. The examples also include a room occupancy sensor 340, capable of determining a current occupancy of a room and transmitting the determined current room occupancy to the environment controller 100. The room comprises the sensors 300 and the controlled appliance 400. However, the environment controller 100 may or may not be present in the room (the environment controller 100 may remotely control the environment of the room, which includes controlling the controlled appliance 400 based on the inputs of the sensors 300).

The aforementioned examples of sensors 300 are for illustration purposes only, and a person skilled in the art would readily understand that other types of sensors 300 could be used in the context of an environment control system managed by the environment controller 100. Furthermore, each environmental characteristic value may consist of either a single value (e.g. current temperature of 25 degrees Celsius), or a range of values (e.g. current temperature from 25 to 26 degrees Celsius).

The temperature, humidity and $CO_2$ sensors are well known in the art, and easy to implement types of sensors. With respect to the occupancy sensor, its implementation may be more or less complex, based on its capabilities. For example, a basic occupancy sensor (e.g. based on ultrasonic or infrared technology) is only capable of determining if a room is occupied or not. A more sophisticated occupancy sensor is capable of determining the number of persons present in a room, and may use a combination of camera(s) and pattern recognition software for this purpose. Consequently, in the context of the present disclosure, a sensor 300 shall be interpreted as potentially including several devices cooperating for determining an environmental characteristic value (e.g. one or more cameras collaborating with a pattern recognition software executed by a processing unit for determining the current number of persons present in the room).

Also represented in FIG. 1 is the controlled appliance 400. Although not represented in FIG. 1 for simplification purposes, the controlled appliance 400 comprises at least one actuation module, and a communication interface for receiving one or more commands from the environment controller 100. The actuation module can be of one of the following type: mechanical, pneumatic, hydraulic, electrical, electronical, a combination thereof, etc. The one or more commands control operations of the at least one actuation module. The one or more commands are transmitted over a communication network via the communication interface 130 of the environment controller 100.

FIG. 2 illustrates an example of a controlled appliance 410, consisting of a VAV appliance. Examples of commands transmitted to the VAV appliance 410 include commands directed to one of the following: an actuation module controlling the speed of a fan, an actuation module controlling the pressure generated by a compressor, an actuation module controlling a valve defining the rate of an airflow, etc. This example is for illustration purposes only, and a person skilled in the art would readily understand that other types of controlled appliances 400 could be used in the context of an environment control system managed by the environment controller 100.

Also represented in FIG. 1 is a user 10. The user 10 provides at least one set point to the environment controller 100. Examples of set points include target environmental characteristic values, such as a target temperature, a target humidity level, a target CO2 level, a combination thereof, etc. The at least one set point is related to the room where the sensors 300 and the controlled appliance 400 are located. Alternatively, the controlled appliance 400 is not located in the room, but the operations of the controlled appliance 400 under the supervision of the environment controller 100 aim at reaching the at least one set point in the room. The user enters the at least one set point via the user interface 140 of the environment controller 100. Alternatively, the user enters the at least one set point via a user interface of a computing device (e.g. a smartphone, a tablet, etc.) not represented in FIG. 1 for simplification purposes; and the at least one set point is transmitted over a communication network and received via the communication interface 130 of the environment controller 100.

FIG. 2 illustrates examples of set points, comprising a target temperature, a target humidity level and a target CO2 level. These examples are for illustration purposes only, and a person skilled in the art would readily understand that other types of set points could be used in the context of an environment control system managed by the environment controller 100. Furthermore, each set point may consist of either a single value (e.g. target temperature of 25 degrees Celsius), or a range of values (e.g. target temperature from 25 to 26 degrees Celsius).

The method 500 comprises the step 505 of executing the neural network training engine 211 (by the processing unit of the training server 200) to generate the predictive model.

The method 500 comprises the step 510 of transmitting the predictive model to the environment controller 100, via the communication interface of the training server 200.

The method 500 comprises the step 515 of storing the predictive model in the memory 120 of the environment controller 100. The predictive model is received via the communication interface 130 of the environment controller 100, and stored in the memory 120 by the processing unit 110.

The method 500 comprises the step 520 of receiving the at least one environmental characteristic value from the at least one sensor 300. The at least one environmental characteristic value is received by the processing unit 110 via the communication interface 130. Step 520 is performed by the control module 114 executed by the processing unit 110.

The method 500 comprises the step 525 of receiving the at least one set point from the user 10. The at least one set point is received by the processing unit 110 via the user interface 140 and/or the communication interface 130. Step 525 is performed by the control module 114 executed by the processing unit 110.

The method 500 comprises the step 530 of executing the neural network inference engine 112 (by the processing unit 110). The neural network inference engine 112 uses the predictive model (stored in memory 120 at step 515) for inferring one or more commands for controlling the appliance 400, based on the at least one environmental characteristic value (received at step 520) and the at least one set point (received at step 525).

The method 500 comprises the step 535 of transmitting the one or more commands to the controlled appliance 400 via the communication interface 130.

The method 500 comprises the step 540 of applying by the controlled appliance 400 the one or more commands received from the environment controller 100.

Steps 530, 535 and 540 are repeated if new parameters are received at steps 520 (one or more new environmental characteristic value) and/or 525 (one or more new set point). Furthermore, configurable thresholds can be used for the parameters received at steps 520 and 525, so that a change in the value of a parameter is not taken into consideration as long as it remains within the boundaries of the corresponding threshold(s). For example, if the parameter is a new current temperature received at step 520, the threshold can be an increment/decrease of 1 degree Celsius in the current temperature. If the parameter is a new target temperature received at step 525, the threshold can be an increment/decrease of 0.5 degree Celsius in the target temperature. Additionally, the control module 114 may discard any new environment characteristic value received at step 520 unless a new set point is received at step 525.

Reference is now made to FIG. 1, and more particularly to the neural network inference engine 112 and the neural network training engine 211.

Various criteria may be taken into consideration for optimizing the one or more commands generated by the environment controller 100 for controlling the appliance 400, based on at least one environmental characteristic value and at least one set point. As previously mentioned, such criteria include a comfort of the people present in the room where the controlled appliance 400 is located, stress imposed on components of the controlled appliance 400 (e.g. mechanical stress, heating stress, etc.), energy consumption of the controlled appliance 400, etc. These criteria are for illustration purposes only, and are not limitative.

The present disclosure aims at providing a mechanism for inferring an optimal set of command(s) for controlling the appliance 400 based on the aforementioned criteria, whatever the at least one environmental characteristic value and the at least one set point may be. The mechanism disclosed in the present disclosure takes advantage of the neural network technology, to "guess" the optimal set of command(s) in operating conditions, based on a model generated during a training phase.

A first type of data used as inputs of the neural network training engine 211 (during a training phase) and the neural network inference engine 112 (during an operational phase) consists of one or more environmental characteristic value(s). Examples of environmental characteristic values have already been described, but the present disclosure is not limited by those examples. A person skilled in the art of environmental control systems would readily adapt the type of environmental characteristic value(s) to a specific type of controlled appliance 400.

A second type of data used as inputs of the neural network training engine 211 (during a training phase) and the neural network inference engine 112 (during an operational phase) consists of one or more set point(s). Examples of set points have already been described, but the present disclosure is not limited by those examples. A person skilled in the art of environmental control systems would readily adapt the type of set point(s) to a specific type of controlled appliance 400.

The output(s) of the neural network training engine 211 (during a training phase) and the neural network inference engine 112 (during an operational phase) consists of one or more commands for controlling the appliance 400. Examples of commands have already been described, but the present disclosure is not limited by those examples. A person skilled in the art of environmental control systems would readily adapt the type of commands to a specific type of controlled appliance 400.

Combinations of at least one environmental characteristic value, at least one set point, and one or more command(s) for the controlled appliance 400, are taken into consideration by the neural network inference engine 112 and the neural network training engine 211. The best combinations can be determined during the training phase with the neural network training engine 211. The best combinations may depend on the type of controlled appliance 400, on criteria for evaluating the adequacy of the one or more command(s), on characteristics of the room where the controlled appliance 400 is located, etc.

Examples of criteria for evaluating the adequacy of the one or more command(s) have already been described, but the present disclosure is not limited by those examples. A person skilled in the art of environmental control systems would readily adapt the criteria to a specific type of controlled appliance 400.

The training phase is used to identify the best combinations of input and output parameters, and only those parameters will be used by the neural network training engine 211 to generate the predictive model used by the neural network inference engine 112. Alternatively, all the available parameters can be used by the neural network training engine 211 to generate the predictive model. In this case, the neural network training engine 211 will simply learn to ignore some of the input parameters which do not have a significant influence on the one or more commands for controlling the appliance 400.

During the training phase, the neural network training engine 211 is trained with a plurality of inputs (each input comprises at least one environmental characteristic value and at least one set point) and a corresponding plurality of outputs (each corresponding output comprises one or more commands for the controlled appliance 400). As is well known in the art of neural network, during the training phase, the neural network implemented by the neural network training engine 211 adjusts its weights. Furthermore, during the training phase, the number of layers of the neural network and the number of nodes per layer can be adjusted to improve the accuracy of the model. At the end of the training phase, the predictive model generated by the neural network training engine 211 includes the number of layers, the number of nodes per layer, and the weights.

The inputs and outputs for the training phase of the neural network can be collected through an experimental process. For example, a plurality of combinations of current temperature and target temperature are tested. For each combination, a plurality of sets of command(s) are tested, and the most adequate set of command(s) is determined based on criteria for evaluating the adequacy. For example, the criteria are comfort for the user and energy consumption. In a first case, the current temperature is 30 degrees Celsius and the target temperature is 22 degrees Celsius. For simplification, purposes, the set of commands only consists in setting the operating speed of a fan of the controlled appliance 400. The following speeds are available: 5, 10, 15, 20 and 25 revolutions per second. For obtaining a quick transition from 30 to 22 degrees Celsius (to maximize the comfort of the persons present in the room) while preserving energy, it is determined experimentally (or theoretically) that the best speed is 20 revolutions per second. In a second case, the current temperature is 24 degrees Celsius and the target temperature is 22 degrees Celsius. For obtaining a transition from 24 to 22 degrees Celsius (the comfort of the persons present in the room is not substantially affected in this case) while preserving energy, it is determined experimentally (or theoretically) that the best speed is 5 revolutions per second (to maximize the energy savings). Thus, the neural network training engine 211 is fed with the following combinations of data: [current temperature 30, target temperature 22, fan speed 20] and [current temperature 24, target temperature 22, fan speed 5].

As mentioned previously in the description, the environmental characteristic values (e.g. current temperature) and set points (e.g. target temperature) can be expressed either as a single value or as a range of values.

Although a single command has been taken into consideration for simplification purposes, several commands may be considered in combination. For example, the speed of the fan may be evaluated in combination with the pressure generated by a compressor of the controlled appliance 400 for evaluating the most adequate set of commands for transitioning from 30 to 22 degrees Celsius and from 24 to 22 degrees Celsius. Furthermore, more than one set point and/or more than one current environmental value may be used. For example, in addition to the target temperature, a target humidity level is fixed, and various sets of command(s) are evaluated based on the criteria (user comfort, energy consumption, etc.) for performing the transition from the current temperature/humidity level to the target temperature/humidity level. Then, still other current environmental value(s) may be taken into consideration (e.g. room occupancy and/or CO2 level) for performing the transition from the current temperature/humidity level to the target temperature/humidity level.

Various techniques well known in the art of neural networks are used for performing (and improving) the generation of the predictive model, such as forward and backward propagation, usage of bias in addition to the weights (bias and weights are generally collectively referred to as weights in the neural network terminology), reinforcement training, etc.

During the operational phase, the neural network inference engine 112 uses the predictive model (e.g. the values of the weights) determined during the training phase to infer an output (one or more commands for controlling the appliance 400) based on inputs (at least one environmental characteristic value received from the sensor(s) 300 and at least one set point received from the user 10), as is well known in the art.

Figure 4:
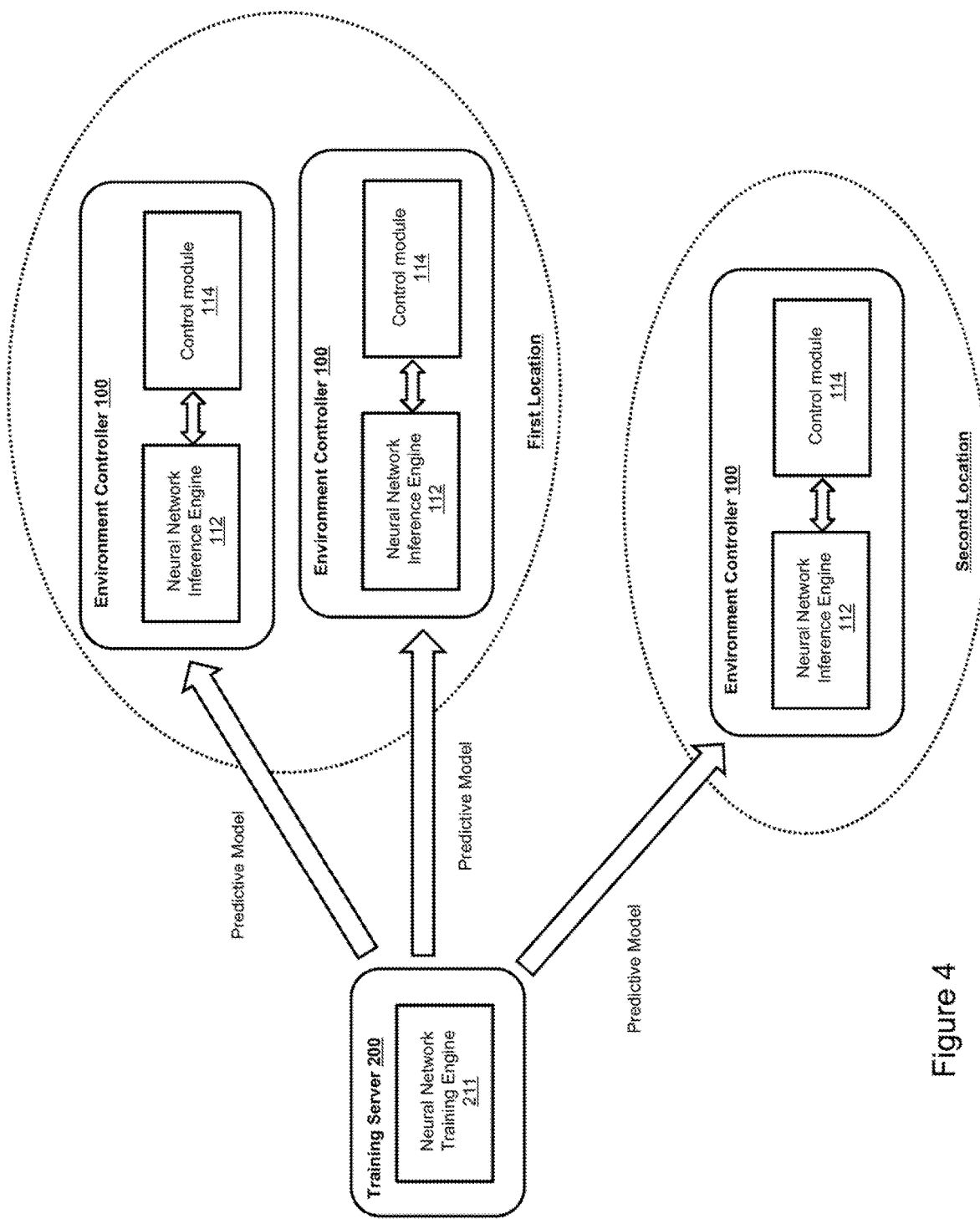
FIG. 4 represents an environment control system where environment controllers implementing the method illustrated in FIG. 3 are deployed.

Reference is now made concurrently to FIGS. 1, 2, 3 and 4, where FIG. 4 illustrates the usage of the method 500 in a large environment control system.

A first plurality of environment controllers 100 implementing the method 500 are deployed at a first location. Only two environment controllers 100 are represented for illustration purposes, but any number of environment controllers 100 may be deployed.

A second plurality of environment controllers 100 implementing the method 500 are deployed at a second location. Only one environment controller 100 is represented for illustration purposes, but any number of environment controllers 100 may be deployed.

The first and second locations may consist of different buildings, different floors of the same building, etc. Only two locations are represented for illustration purposes, but any number of locations may be considered.

Each environment controller 100 represented in FIG. 4 interacts with at least one sensor 300, at least one user 10, and at least one controlled appliance 400, as illustrated in FIG. 1.

The environment controllers 100 correspond to the environment controllers represented in FIG. 1, and execute both the control module 114 and the neural network inference engine 112. Each environment controller 100 receives a predictive model from the centralized training server 200 (e.g. a cloud based training server 200 in communication with the environment controllers 100 via a networking infrastructure, as is well known in the art). The same predictive model is used for all the environment controllers. Alternatively, a plurality of predictive models is generated, and takes into account specific operating conditions of the environment controllers 100. For example, a first predictive model is generated for the environment controllers 100 controlling a first type of appliance 400, and a second predictive model is generated for the environment controllers 100 controlling a second type of appliance 400.

FIG. 4 illustrates a decentralized architecture, where the environment controllers 100 take autonomous decisions for controlling the appliances 400, using the predictive model as illustrated in the method 500.

Figure 5:
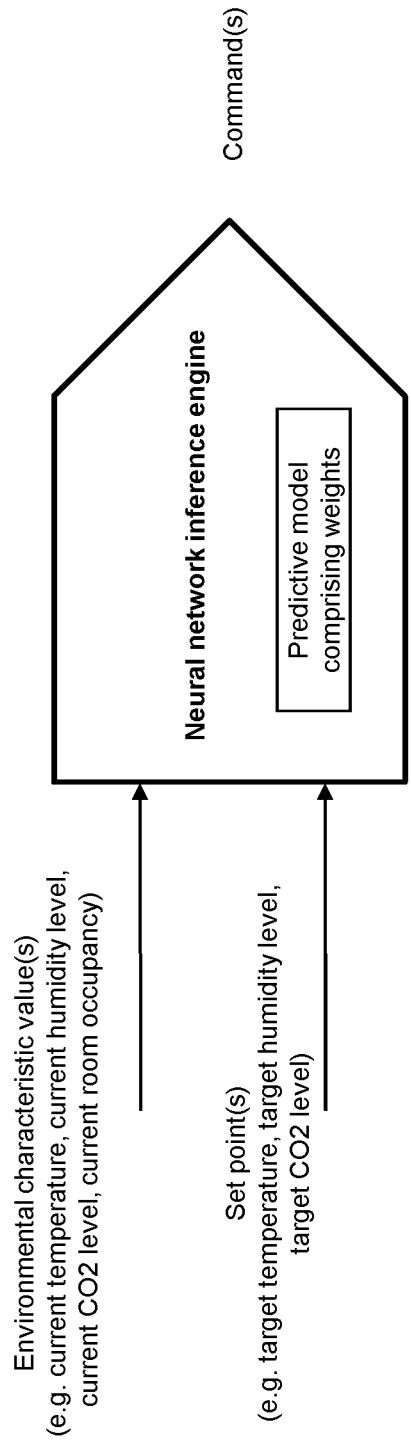
FIG. 5 is a schematic representation of a neural network inference engine executed by the environment controller of FIGS. 1 and 2.

Reference is now made to FIG. 5, which illustrates the aforementioned neural network inference engine with its inputs and its output. FIG. 5 corresponds to the neural network inference engine 112 executed at step 530 of the method 500, as illustrated in FIGS. 1 and 3.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. An environment controller, comprising:
   a communication interface;
   memory for storing a predictive model generated by a neural network training engine, the predictive model comprising weights of a neural network determined by the neural network training engine; and
   a processing unit comprising at least one processor for:
      receiving via the communication interface a current temperature, a current humidity level and a current room occupancy;
      receiving via one of the communication interface and a user interface of the environment controller a target temperature;
      executing a neural network inference engine, the neural network inference engine implementing a neural network using the predictive model for inferring an output based on inputs, the output comprising one or more command for controlling an appliance, the inputs comprising the current temperature, the current humidity level, the current room occupancy and the target temperature; and
      transmitting the one or more command to the controlled appliance via the communication interface.

2. The environment controller of claim 1, wherein the controlled appliance consists of a Variable Air Volume (VAV) appliance.

3. The environment controller of claim 1, wherein the one or more command for controlling the appliance include at least one of the following: a command for controlling a speed of a fan, a command for controlling a pressure generated by a compressor, and a command for controlling a rate of an airflow through a valve.

4. The environment controller of claim 1, wherein the processing unit further receives via the communication interface at least one additional environmental characteristic value; and wherein the inputs of the neural network inference engine further comprise the at least one additional environmental characteristic value.

5. The environment controller of claim 4, wherein the at least one additional environmental characteristic value comprises a current carbon dioxide ($CO_2$) level.

6. The environment controller of claim 1, wherein the processing unit further receives via one of the communication interface and the user interface at least one additional set point; and wherein the inputs of the neural network inference engine further comprise the at least one additional set point.

7. The environment control system of claim 6, wherein the at least one additional set point comprises at least one of the following: a target humidity level and a target $CO_2$ level.

8. The environment controller of claim 1, wherein the processing unit further receives via the communication interface a current carbon dioxide ($CO_2$) level and further receives via one of the communication interface and the user interface a target $CO_2$ level; and wherein the inputs of the neural network inference engine further comprise the current $CO_2$ level and the target $CO_2$ level.

9. The environment control system of claim 1, wherein the current room occupancy consists of a determination whether the room is occupied or not, or consists of a number of persons present in the room.

10. A method for inferring via a neural network one or more command for controlling an appliance, the method comprising:
   storing a predictive model generated by a neural network training engine in a memory of an environment controller, the predictive model comprising weights of a neural network determined by the neural network training engine;
   receiving by a processing unit of the environment controller via a communication interface of the environment controller a current temperature, a current humidity level and a current room occupancy;
   receiving by the processing unit via one of the communication interface and a user interface of the environment controller a target temperature;
   executing by the processing unit a neural network inference engine, the neural network inference engine implementing a neural network using the predictive model for inferring an output based on inputs, the output comprising the one or more command for controlling the appliance, the inputs comprising the current temperature, the current humidity level, the current room occupancy and the target temperature; and
   transmitting by the processing unit the one or more command to the controlled appliance via the communication interface.

11. The method of claim 10, wherein the controlled appliance consists of a Variable Air Volume (VAV) appliance.

12. The method of claim 10, wherein the one or more command for controlling the appliance include at least one of the following: a command for controlling a speed of a fan, a command for controlling a pressure generated by a compressor, and a command for controlling a rate of an airflow through a valve.

13. The method of claim 10, further comprising receiving by the processing unit via the communication interface at least one additional environmental characteristic value; and wherein the inputs of the neural network inference engine further comprise the at least one additional environmental characteristic value.

14. The method of claim 13, wherein the at least one additional environmental characteristic value comprises a current carbon dioxide ($CO_2$) level.

15. The method of claim 10, further comprising receiving by the processing unit via one of the communication interface and the user interface at least one additional set point; and wherein the inputs of the neural network inference engine further comprise the at least one additional set point.

16. The method of claim 15, wherein the at least one additional set point comprises at least one of the following: a target humidity level and a target CO2 level.

17. The method of claim 10, further comprising receiving by the processing via the communication interface a current carbon dioxide (CO2) level and further receiving via one of the communication interface and the user interface a target CO2 level; and wherein the inputs of the neural network inference engine further comprise the current CO2 level and the target CO2 level.

18. The method of claim 10, wherein the current room occupancy consists of a determination whether the room is occupied or not, or consists of a number of persons present in the room.

19. A non-transitory computer program product storing instructions executable by a processing unit of an environment controller, the execution of the instructions by the processing unit of the environment controller providing for inferring via a neural network one or more command for controlling an appliance by:

storing a predictive model generated by a neural network training engine in a memory of the environment controller, the predictive model comprising weights of a neural network determined by the neural network training engine;

receiving by the processing unit via a communication interface of the environment controller a current temperature, a current humidity level and a current room occupancy;

receiving by the processing unit via one of the communication interface and a user interface of the environment controller a target temperature;

executing by the processing unit a neural network inference engine, the neural network inference engine implementing a neural network using the predictive model for inferring an output based on inputs, the output comprising the one or more command for controlling the appliance, the inputs comprising the current temperature, the current humidity level, the current room occupancy and the target temperature; and transmitting by the processing unit the one or more command to the controlled appliance via the communication interface.

* * * * *